United States Patent [19]

Shaposka et al.

[11] Patent Number: 5,158,630
[45] Date of Patent: Oct. 27, 1992

[54] TOTAL CONTAINMENT WELDING OR PLASTIC TUBES

[75] Inventors: John B. Shaposka; Dudley W. Spencer, both of Wilmington, Del.

[73] Assignee: Denco, Inc., Wilmington, Del.

[21] Appl. No.: 604,979

[22] Filed: Oct. 29, 1990

Related U.S. Application Data

[63] Continuation-in-part of Ser. No. 569,855, Aug. 20, 1990.

[51] Int. Cl.⁵ .............................................. B29C 65/20
[52] U.S. Cl. ................................... 156/158; 156/159; 156/304.2; 156/304.5; 156/304.6; 156/515; 156/518; 156/530
[58] Field of Search .................. 156/158, 304.2, 304.5, 156/304.6, 251, 258, 515, 518, 530, 159

[56] References Cited

U.S. PATENT DOCUMENTS

| | | | |
|---|---|---|---|
| 3,552,265 | 1/1971 | Lucas | 156/258 |
| 4,369,779 | 1/1983 | Spencer | 156/304.2 |
| 4,507,119 | 3/1985 | Spencer | 156/304.2 |
| 4,516,971 | 5/1985 | Spencer | 156/304.2 |
| 4,521,263 | 6/1985 | Benin | 156/304.2 |
| 4,737,214 | 4/1988 | Leurink | 156/158 |
| 4,753,697 | 6/1988 | Shaposki et al. | 156/304.2 |
| 4,770,735 | 9/1988 | Shaposka et al. | 156/304.2 |
| 4,793,880 | 12/1988 | Shaposka et al. | 156/304.2 |
| 4,832,773 | 5/1989 | Shaposka et al. | 156/304.2 |
| 4,897,138 | 1/1990 | Shaposka et al. | 156/304.2 |
| 4,913,756 | 4/1990 | Shaposka et al. | 156/304.2 |
| 4,933,036 | 6/1990 | Shaposka et al. | 156/304.2 |

*Primary Examiner*—Caleb Weston
*Attorney, Agent, or Firm*—Connolly & Hutz

[57] ABSTRACT

Plastic tubes are welded by placing a pair of tubes in a pair of aligned holders with each tube folded toward itself. A wafer is movably mounted in the gap between the tubes and is heated to cause the ends of the tubes to melt without actually cutting through the tubes. The melted ends of opposed tubes can be pressed into contact with each other to form a welded connection. In a variation a pair of cutting blades cut the folded ends of the tubes and the cut ends are then melted by a wafer and subsequently pressed into contact with each other.

31 Claims, 4 Drawing Sheets

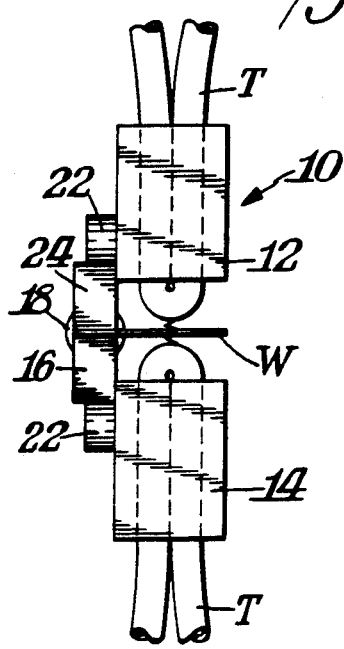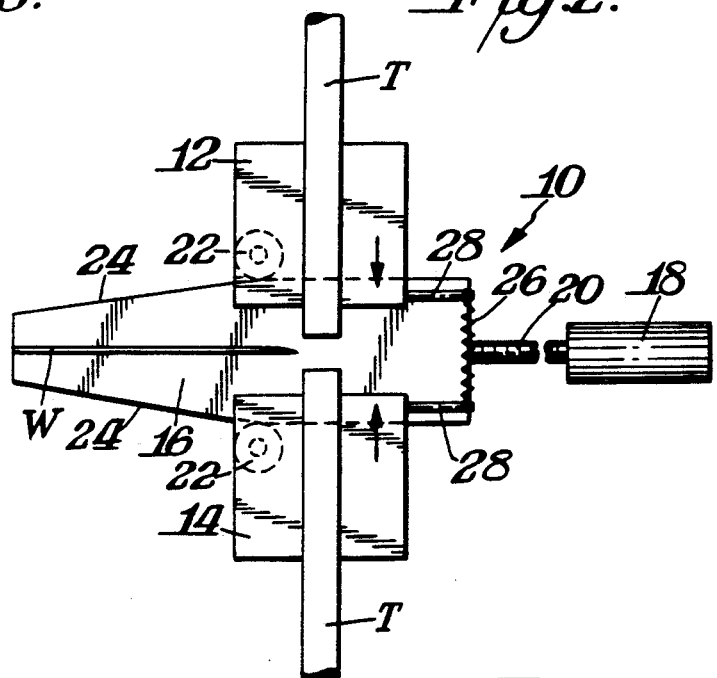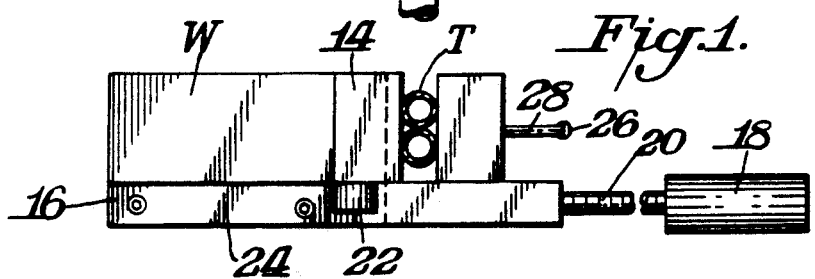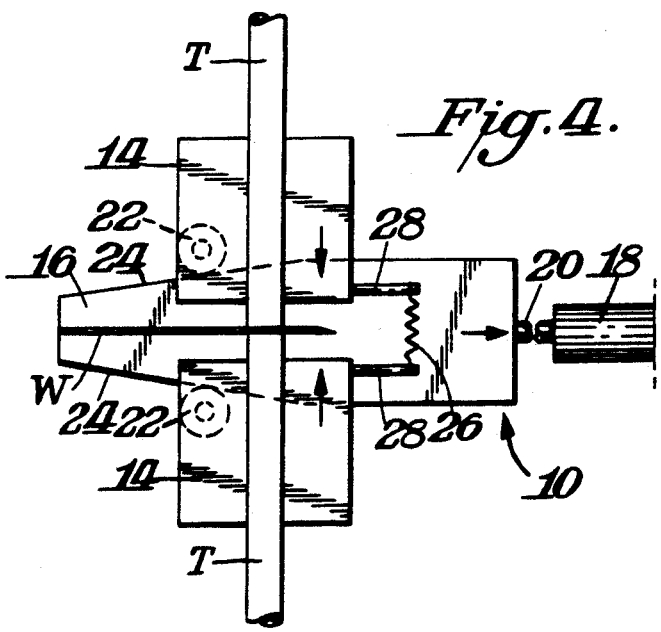

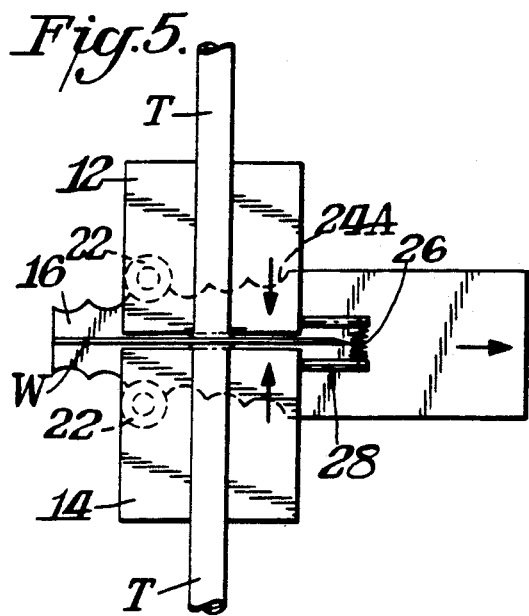
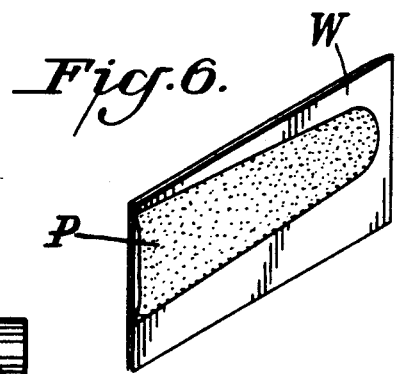
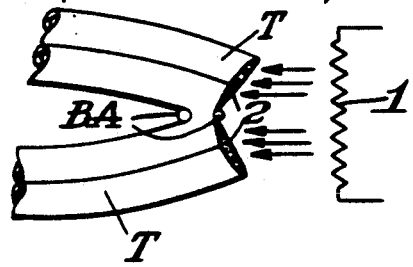
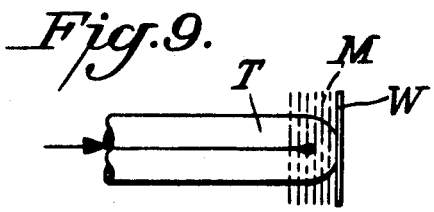
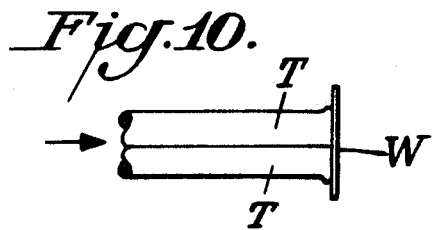

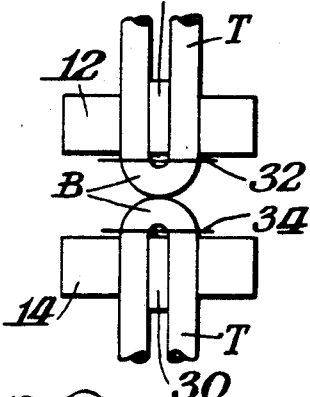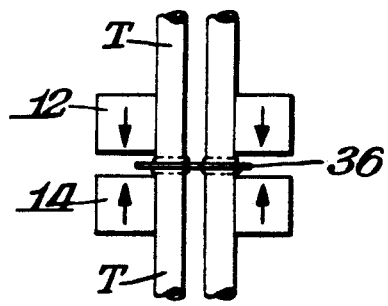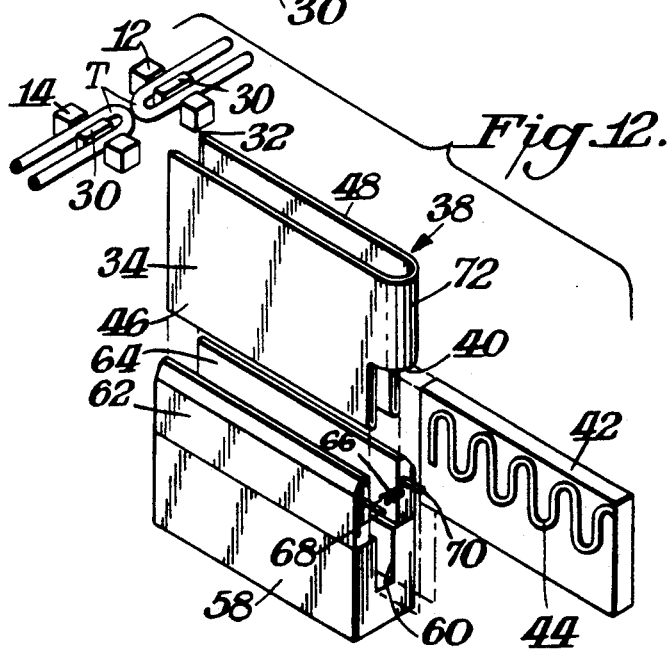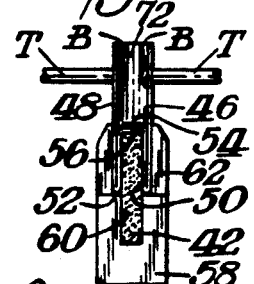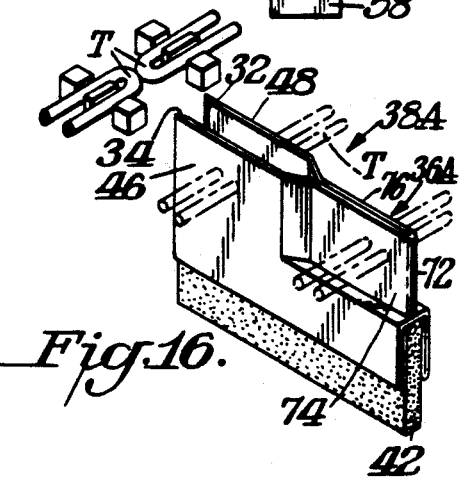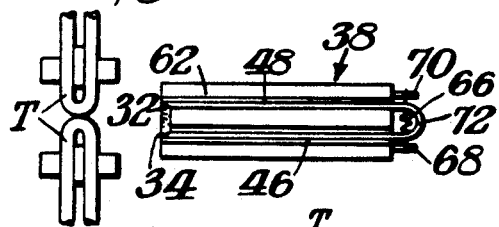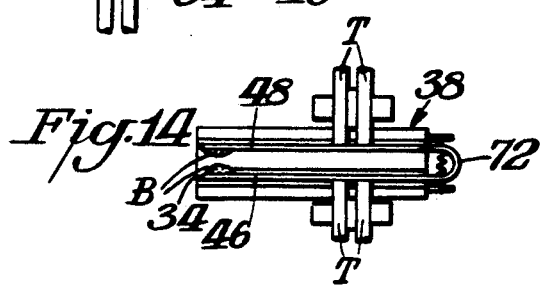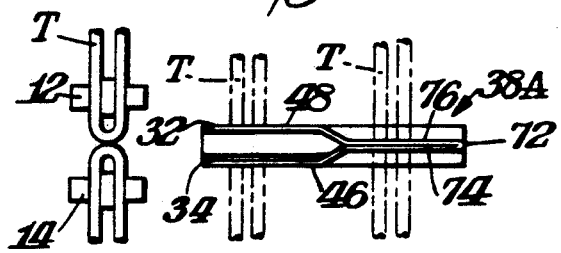

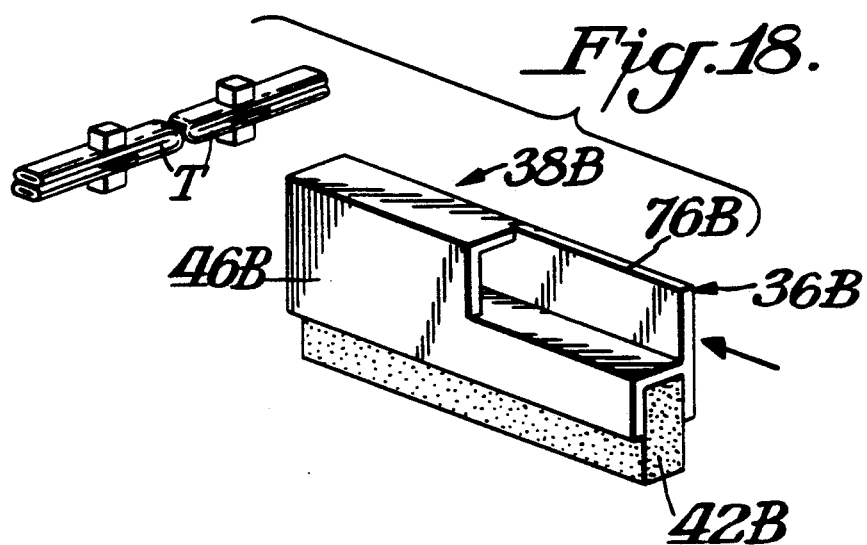
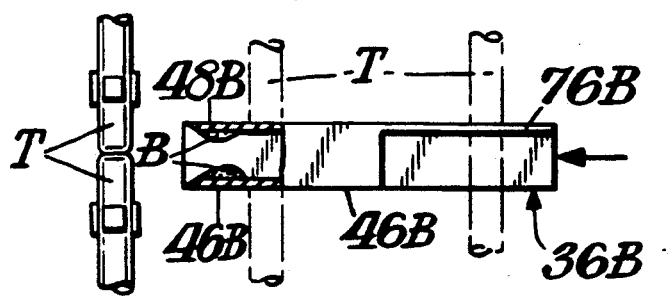
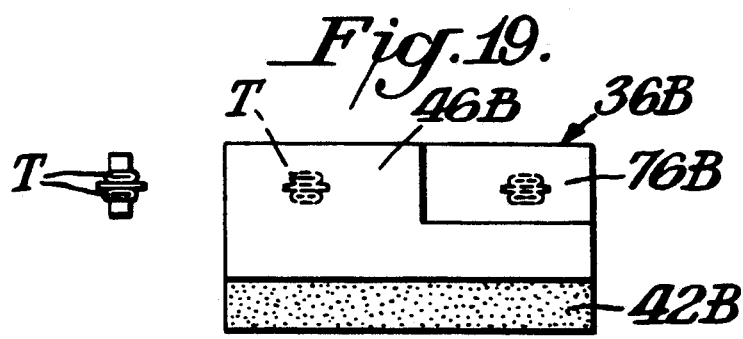

TOTAL CONTAINMENT WELDING OR PLASTIC TUBES

CROSS-REFERENCE TO RELATED APPLICATIONS

This application is a continuation in part of application Ser. No. 569,855 filed Aug. 20, 1990, entitled "Sterile Entry/Exit Total Containment Process For Closed Systems Using Plastic Tubes".

BACKGROUND OF INVENTION

The present invention relates to the sterile and total containment welding techniques for fluid filled plastic tubes that control bacterial necrosis through rheological dynamics.

Prior patents such as our U.S. Pat. No. 4,793,880 and U.S. Pat. Nos. 4,610,670 and 4,369,779 by co-inventor Dudley W. Spencer disclose processes that once the process starts, have no control of the interrelated series of events leading to a sterile connection. For example, no attempt is made, other than setting the upper temperature limit of the cutting means, to control the welding process to guarantee sterility each time a weld is made. Variables such as Temperature drop of the blade from cutting the plastic or fluids
Plastic Rheology
Debri control
Weld strength
Pin holes within the joint
Lumen occlusion
Bacterial Morphology & necrosis
are all out of control during the critical phases of process dynamics. Moreover, the processes leave two leaky stub ends that are unacceptable for handling dangerous fluids.

Our U.S. Pat. No. 4,753,697 solved the leaky stub-end problem, but no attempt was made to gain control of the process dynamics.

SUMMARY OF INVENTION

An object of this invention is to provide a process and apparatus which has gained control of the welding process by eliminating the cutting requirements and substituting a plastic melt-wiping process that raises the control levels of Plastic rheology
Bacteria necrosis
Debri control
Lumen occlusion
Weld strength
to a point where sterile and total containment performance is assured.

A further object of this invention is to provide reliability of sterile and total containment hitherto unobtainable in the prior art.

In accordance with this invention the tubes to be welded together are to be placed in a pair of aligned holders with each tube folded toward itself. A heated wafer is mounted for movement in the gap between the tubes. A cam arrangement is provided between the tube holders and the wafer mounting device so that the tubes are continuously moved toward each other at a controlled rate as the wafer moves between them. In this manner, the tubes are melted by a wiping action with respect to the heated wafer rather than by having the wafer physically cut through the tubes.

In an alternative form of this invention the bent ends of the tubes are pre-cut by a pair of blades prior to the melting step.

THE DRAWINGS

FIG. 1 is a side elevation view of a total containment welding system in accordance with this invention;

FIG. 2 is a top plan view of the system shown in FIG. 1;

FIG. 3 is a front elevation view of the system shown in FIGS. 1-2;

FIG. 4 is a top plan view of the system shown in FIGS. 1-3 in a later phase of operation;

FIG. 5 is a top plan view of a modified form of system in accordance with this invention;

FIG. 6 is a perspective view of a wafer usable with this invention;

FIG. 7 is a top plan view of a prior art technique;

FIGS. 8-10 are top plan views, schematically illustrating the wafer and a tube during the various stages in which melting occurs in the tube;

FIGS. 11A and 11B are top plan view schematically showing an alternative form of this invention;

FIG. 12 is a perspective view showing an alternative form of wafer arrangement for practicing the operation of FIG. 11A;

FIGS. 13-14 are plan views schematically showing use of the wafer of FIG. 12 in different phases of operation;

FIG. 15 is a left end elevation view of the wafer shown in FIG. 13;

FIG. 16 is a perspective view of a modified form of wafer capable of performing the operations in both FIGS. 11A and 11B;

FIG. 17 is a top plan view of the wafer shown in FIG. 16;

FIG. 18 is a perspective view of still another modified form of wafer in accordance with this invention;

FIG. 19 is a side elevation view showing the wafer of FIG. 18; and

FIG. 20 is a top plan view showing the wafer of FIGS. 19-20.

DETAILED DESCRIPTION

The present invention is based upon the techniques described in our U.S. Pat. No. 4,753,697, the details of which are incorporated herein by reference thereto. The basic difference of the present invention from the '697 patent is that with the present invention there is a wiping action between the heating means and the plastic tubes. The '697 patent, however, is basically concerned with two methods of achieving a weld. The first method is a slit-cut and radiant heating process that eliminates the need for a wafer. In order to achieve bacterial necrosis at the inner wall, the radiant heat tends to melt the plastic to a point where rheology control is lost and thereby process reliability is compromised. The second method is a melt process where the heating means is stationary. As shown in FIGS. 17-20 of the '697 patent the heated wafer is stationary during the melting process and then is moved away to permit butt welding. The heat reservoir tends to become exhausted through melting through the plastic such that the temperatures required at the inner walls to kill the bacteria are not as reliable as would be desired. Raising the temperature of the heating means would tend to be counter-productive in that plastic rheology control is lost and degraded plastic is deposited at the weld site. FIG. 7, for example, illustrates such technique wherein the radiant heater 1 heats the cut ends 2 of the plastic tubes T. Bacteria is formed as indicated by the reference numeral BA.

FIGS. 8-10 illustrate the primary actions on which the present invention is based with respect to one of the tubes. As shown therein the tube T is folded toward itself and is disposed in proximity to a wafer W which heats the folded end of tube T. As the tube and wafer move closer to each other, a melting of the tube results as illustrated by the shade lines M of FIG. 9. Finally, the folded end is completely melted and the tube is disposed against or very near to the wafer W. Accordingly, the hollow interior of the two aligned tube sections T,T are exposed by a melting or wiping action rather than by having the wafer cut through each tube as was practiced in the prior art.

FIGS. 1-3 illustrate a total containment welding device or system 10 in accordance with this invention. As shown therein, a pair of holders 12,14 are provided into which the tubes T,T are mounted and clamped in a known manner. Holders 12,14 are mounted for relative movement toward each other as indicated by the arrows. The wafer W is mounted on a movable unit 16 which is driven in any suitable manner such as by motor 18 attached to drive shaft 20 connected to unit 16. In the first stage of operation the wafer W is heated until it reaches the bacteria killing temperature of at least about 500° F. The mounting unit 16 then begins to move toward the right as shown in FIG. 2 at a speed controlled by the melt rate of the plastic of tubes T. Each tube holder is provided with a contact member or cam 22 in the form of a roller which is mounted for positioning against the tapered edges 24 of wafer holder or mount 16. Holders 12 and 14 are urged toward each other in any suitable manner, such as by the influence of spring 26 secured to posts 28 on each holder. Thus, as mounting unit 16 moves toward the right the spring 26 urges the cams or rollers 22 to maintain contact with the edges 24 of mounting unit 16. As a result, the tubes T are moved toward each other in a continuous manner at a predetermined rate of advance. The coordinated controlled movement of the tubes toward each other while the wafer is moving is a characteristic quite distinct from the '697 patent.

FIG. 4 illustrates the condition of the various elements of device 10 when rollers 22 are about way down the edges 24 of mounting unit 16. By this arrangement the tubes T,T are maintained in intimate contact with (or at the desired close spacing to) the wafer W from the moment the wafer first enters the gap between the aligned tubes until the wafer has completely passed through that gap. During this movement, the tube ends are gradually melted as illustrated in FIGS. 8-10. An advantage is that the movement is all in one direction.

After the wafer W has passed the tubes T,T the melted ends of the aligned tube sections are pressed together to create a weld. The welded tubes are then removed from the clamps on holder 12,14 and the wafer may be replaced by a new wafer or the old wafer may be cleaned and re-used. The transverse bar or mounting unit 16 is then returned to its start position illustrated in FIGS. 1-3.

The welding process is thus characterized as not cutting the tubes to make a weld. The action is a melt-wipe process where the rate of wafer and tube advance is based upon the melt rate of the plastic. The wafer acts as a debri collector and melt pull seal control means.

FIG. 6 illustrates a wafer W with the melted plastic P from the tubes T adhered to each side of wafer W. Advantageously this residue or plastic P will fall off wafer W without the need for any special cleaning. Accordingly, if desired, the same wafer may be reused for more than one process.

FIG. 5 illustrates a variation of this invention wherein a pulsating effect is created as the wafer moves between the tubes T. This pulsating effect is created by forming the edges 24A in an undulated manner with a series of smooth recesses so that the tubes are pushed close together while the rollers 22 enter the recesses and then drawn slightly apart while rollers 22 exit from each recess. This pulsating movement cuts both the time and distance required for an effective operation. For example, an operation requiring a length of five inches in the embodiment of FIGS. 1-3 would be reduced to only two inches in the embodiment of FIG. 5.

The melt-wipe action of this invention can be facilitated by a variation which is illustrated in principle in FIGS. 11A and 11B. As shown therein, a pair of tubes T,T would be mounted in holders 12,14 as previously described. A spacer bar 30 could be positioned at the bent ends of the tubes. It is to be understood that such spacer bar could also be positioned in the embodiments of the invention previously described. The practice of the invention of FIGS. 11A and 11B involve a pre-cut action so that less time is required to effect a melting of the tube ends. This is accomplished by providing a pair of blades 32,34 which would move along paths spaced from each other so as to cut the bent ends B of the tubes in a preliminary operation as illustrated in FIG. 11A. After the bent ends B have been cut and removed, a wafer 36 would then pass in the gap between the cut tubes simultaneously with the movement of the wafer in the gap the tubes would be urged toward each other as previously described. This concept could be practiced by having blades 32 and 34 as separate spaced members which move jointly to simultaneously cut both tubes, or by using a single blade to sequentially cut each tube. Additionally, the blades 32,34 could be mounted on separate drives or could be mounted on the same drive as wafer 36. When blades 32,34 are mounted on the same drive or mounting unit as wafer 36 that portion of the mounting unit would have straight sides so that the tubes T,T would remain stationary and not be moved toward each other as is done when the melt wafer 36 passes between the tubes.

FIGS. 12-15 illustrate one manner of practicing the embodiment of the invention conceptually illustrated in FIGS. 11A and 11B. As shown therein the pair of tubes T,T are mounted in holders 12,14 with a spacer bar 30 located at the bent portion of the tubes. Blades 32,34 comprise the beveled lead edges of a copper sheath type wafer 38 which is bent at its trailing end to provide a set of spaced walls 46,48 which terminate at sharp edges to comprise the blades 32,34. A notch 40 is located at the bent trailing end of sheath 38. A suitable heating device, such as ceramic heater 42, having heating element 44 thereon is telescoped into the space between the opposed walls of sheath 38. As best shown in FIG. 15 side walls 46,48 of sheath 38 include extensions 50,52 which are bent upwardly against the main portions of side walls 46,48 and then terminate in horizontal flanges 54,56 which overlap each other. This arrangement effectively creates a shield above ceramic heater 42 to keep plastic material from the cut ends B,B from dripping on heater 42.

The sheath 38 is mounted on a mounting block 58 which has a U-shaped recess 60 for receiving the lower portion of heater 42. Walls 62,64 of mounting block 58 are spaced from each other, but are urged toward each other by spring clips which can take any suitable form. For example, as illustrated in FIG. 12, the urging action is achieved by mounting a spring 66 to a pair of pins 68,70 on the respective walls 62,64. The spring clips press against heater 42 to assure that the heater will remain mounted in place. The resulting unit would be positioned with respect to holders 12,14 so that the heated cutting edges or blades 32,34 are in line with tubes T,T. Thus, when the unit is moved into contact with the bent ends a cutting and melting action begins which continues until the cutting edges 32,34 have completely passed through the bent ends. The bent ends in turn are trapped in the space between walls 46,48 and captured therein by the bight 72 joining the walls 46,48. The material from the cut ends B,B thus remains with the unit as the unit moves away from the tubes. The tubes would then be urged toward each other in a movement coordinated with the forward movement of wafer 36 through the space between the tubes T,T, as previously described. FIG. 13 for example, illustrates the pre-cutting unit 38 in its position before the cutting action takes place. FIG. 14 illustrates the cutting unit after the bent ends B,B have been cut thereby leaving the exposed ends of tubes T,T in a squared off condition.

FIGS. 16-17 illustrate a variation of this invention wherein the wafer 36 is integral with the pre-cutting unit. As shown therein, the copper sheath 38A would have the same general construction as in the embodiment of FIG. 12. Side walls 46,48 however, would include extensions 74,76 which would be by closer by converging and preferably being in contact with each other. Extensions 74,76 terminate in the bight portion 72. The extensions 74,76 would jointly function as the wafer 36A in that the side walls 74,76 would be heated by ceramic heater 42 in the same manner that side walls 46,48 are heated for the pre-cutting operation. The unit would be mounted on a wafer mounting unit such as unit 16 as previously described. Thus the tubes T,T would move to move toward each other at the transition where sheath 38 has its side walls 46,48 spaced from each other and then converge to where its side walls 74,76 are juxtaposed each other. The various stages of tubes T,T are illustrated along different portions of relative travel of sheath 38A.

FIGS. 18-20 show a further modification of this invention involving the unitary pre-heating and melt-wipe wafer 36B. Wafer 36B is similar in construction to wafer 36A, except that instead of having a pair of walls at the wipe-melt section, such as walls 74,76 in FIG. 16. A portion of one wall is cut out or notched leaving only a single wall 76B which functions to effect the melt-wipe action. Thus, the wafer 36B would still include a sheath 38B having a pair of walls 46B,48B with the heater 42B mounted in the lower portion between the walls. As shown in FIG. 18 the tubes T,T would be initially bent and would be arranged in the path of the cutting portion of the wafer formed by the beveled lead edges of walls 46B and 48B. Wafer 36B moves toward tubes T,T as shown in the left-hand most portion of FIGS. 19-20. As then shown in phantom, the tubes would be cut so as to be squared off and finally wall 76B would effect a melt-wipe action as shown in the extreme right-hand portion of FIGS. 19-20 so that the tube sections could then be welded together.

It is to be understood that the various aspects of this invention may be practiced with the tubes bent along a vertical axis or along a horizontal axis. Thus the tubes could take the position of bend shown in FIG. 12 or the position shown in FIG. 18.

The melt-wipe concept of this invention is a distinctly different process from the cut and shift teachings of U.S. Pat. Nos. 4,369,779, and 4,610,670 to make a sterile connection. In addition, the '779 and '670 patents also teach the concept of a continuous "melt pool" at the plastic/heating means interface to exclude bacteria from the weld. The present invention, however, teaches that a continuous melt pool is not required provided the weld site remains in close proximity to the heating means, but not necessarily touching.

With this invention the plastic residue (can be removed from the heating means or wafer by keeping the wafer above the PVC degradation temperature (350°) to allow the dioctalphlate to evaporate. The residual PVC char will then fall away from the wafer leaving a clean surface. The significance of this finding is that the wafer need not be changed after each weld as is currently the practice.

Where the invention is practiced for blood bag size tubing (0.156" O.D.) the melt-wipe footprint required to make a strong weld without a significant tube flange is 2" which is an acceptable length for the heated wafer. For CAPD tubing (0.215" O.D.) the footprint is 5 inches. To reduce this length to 2 inches or less the "touch and lift" technique is used. The concept of not needing a continuous "melt pool" makes this idea practical.

Although a smooth surface wafer is preferred, the melt-wipe footprint can also be reduced by roughening the surface of the wafer that contacts the PVC. In essence all the roughening methods try to act as a heat file. The following are possible methods listed in declining order of effectiveness:
Nail file;
Broach;
Perforated holes;
Slots;
Rough electroplating;
Rough sandblasting;
Acid etch;
Coining.

The scarified surfaces also negate the charred PVC release feature that can be achieved with a smooth wafer surface. For this reason, our preferred embodiment is a smooth surfaced wafer combined with the touch and lift process.

The "touch and lift" concept works because as the PVC melts, (when in contact with the wafer) it preferentially adheres to the copper wafer more tenaciously than the parent PVC. When the PVC is lifted away from the wafer, the tenacious hold of the PVC on the wafer and the surface tension within the melt pool pulls the PVC debris away from the weld site thus aiding in the debris accumulation on the wafer.

The concepts of this invention may be practiced with the techniques of parent application serial no. 569,855, the details of which are incorporated herein by reference thereto.

The present invention makes it thus possible to achieve the following objects:

Non-cutting of tubes: all process control is accomplished by melt-wiping;
A one way wiping action to control plastic rheology
Control of plastic debri;
Non re-contamination of joining site;
Melt pool sealing control;
A linear (non-retraceable) action;
Minimizing di-octal-phlate aerosols;
On board feed back control of
 Heating means initial temperature,
 Heating means heat sink,
 Heating means traverse rate,
 Folded tube advance rate into the heating means;
All areas of the exposed tube surfaces treated uniformly;
Measurement of the heating means at tube exit to ensure that bacteria necrosis temperatures have been achieved;
A means of controlling the plastic melting, rheology and deposition rate to remove excess away from the weld site;
A means of controlling the tube exterior flange size for optimum strength and aesthetics;
A means of controlling the melting in the area of the tube lumen to avoid occlusion and minimize the force required to re-open the lumen;
A means of providing total containment;
A means for providing multiple welding pockets for adding or subtracting plastic (pharmaceutical) consumables.

Accordingly, it is possible to use the present invention for the following applications and consumables:

Applications: Blood Processing, CAPD—Renal, Plasma pherisis, Fractionation, Urinary drainage, Biotech, Hospital Pharmacea, General Bio & Chem lab usage, Chemo-therapy, TPN, IV solution additions etc.

Consumables: Filters, Membranes, Assays, Nutrients, Innoculants, Buffers, Antibiotics, Isotopes, Hepatitis & AIDS indicators, Samples etc.

What is claimed is:

1. A total containment welding system for plastic tubes comprising a pair of aligned tube holders for holding a pair of plastic tubes in line with each other, a wafer capable of being heated to an elevated temperature for melting the plastic tubes when the plastic tubes are in contact with or close to said wafer, said wafer being mounted on a wafer mounting unit for moving said wafer in the gap between the plastic tubes in a transverse direction perpendicular to the aligned plastic tubes, and means for urging said holders toward each other simultaneously with the movement of said wafer from at least the time the plastic tubes initially contact the wafer to maintain the plastic tubes in their proper contacting position with said wafer as said wafer moves through said gap to melt the ends of the plastic tubes and to urge the melted ends of the plastic tubes into contact with each other to weld the plastic tubes together.

2. The system of claim 1 including control means for coordinating the movement of said holders toward each other in accordance with the transverse movement of said wafer.

3. The system of claim 2 wherein said control means comprises a pair of inclined edges on said wafer mounting unit, said inclined edges diverging away from each other from the trailing end to the lead end of said wafer, and each of said holders having a contact member disposed against a respective one of said edges whereby said edges act as stop means to limit the movement of said holders toward each other.

4. The system of claim 3 wherein said wafer is mounted midway between said edges.

5. The system of claim 4 wherein said contact members are rollers.

6. The system of claim 5 wherein said means for urging said holders toward each other comprises a spring mounted to each of said holders to create a resilient force.

7. The system of claim 6 including means to create a pulsating movement of said holders toward each other.

8. The system of claim 7 wherein said edges are undulated to comprise said means to create a pulsating movement.

9. The system of claim 3 including means to create a pulsating movement of said holders toward each other.

10. The system of claim 9 wherein said edges are undulated to comprise said means to create a pulsating movement.

11. The system of claim 1 including a pre-cutting unit mounted upstream of said wafer for cutting the adjacent portions of the tubes before said wafer enters said gap.

12. The system of claim 11 wherein said pre-cutting unit includes a pair of spaced cutting edges mounted on a mounting block for joint movement to simultaneously cut both plastic tubes.

13. The system of claim 12 wherein a heater is located on said mounting block between said spaced cutting edges, and a shield being over said heater.

14. The system of claim 13 wherein said wafer is an integral extension of said cutting edges.

15. The system of claim 14 including a heat conductive sheath, said sheath having a pair of spaced side walls having leading edges, said leading edges comprising said cutting edges, and the lower portions of said side walls being up-turned and overlapping each other to form said shield over said heater.

16. The system of claim 15 wherein said side walls converge toward and contact each other remote from said cutting edges to comprise said wafer.

17. The system of claim 13 including a heat conductive sheath, said sheath having a pair of spaced side walls heaving leading edges, said leading edges comprising said cutting edges, and the lower portions of said side walls being up-turned and overlapping each other to form said shield over said heater.

18. A tube end removal unit for removing the ends of aligned and spaced plastic tubes to facilitate the butt welding of the plastic tubes comprising a heat conductive sheath, said sheath having a pair of spaced side walls terminating in leading edges, said leading edges comprising cutting blades for cutting through the plastic tubes, a heater located between said spaced side walls of said sheath, and a shield between said side walls mounted over said heater.

19. The unit of claim 18 wherein said sheath is mounted on a mounting block, said heater being on said mounting block, said mounting block including a pair of upstanding side walls resiliently biased toward each other, and a portion of said heater being mound between said mounting block side walls.

20. The unit of claim 19 wherein said side remote from said leading edges, and said contacting side walls comprising a wafer.

21. The unit of claim 19 wherein the lower portions of said side walls of said sheath are up-turned and overlap each other to comprise said shield.

22. The unit of claim 20 wherein said side walls of said sheath converge toward and contact each other remote from said leading edges, and said contacting side walls comprising a wafer.

23. The unit of claim 19 wherein the trailing end of said sheath comprises a wafer, and said leading edges being beveled.

24. The unit of claim 23 wherein one of said side walls is notched, and the other of said side walls comprising said wafer.

25. The unit of claim 18 wherein the lower portions of said side walls of said sheath are up-turned and overlap each other to comprise said shield.

26. A method of welding a pair of hollow plastic tubes comprising mounting the tubes in alignment with each other in aligned tube holders which are spaced from each other with a gap being between the tube ends, heating a wafer, moving the wafer through the gap, simultaneously urging the ends of the tubes against the wafer throughout the movement of the wafer through the gap with the wafer being maintained in contact with and melting the ends of the tubes as the wafer is moving through the gap from at least the time the ends of the tubes initially contact the wafer to melt the ends of the tubes by the moving wafer and thereby expose their hollow interiors by a melt-wipe procedure, and pressing the melted ends of the aligned tubes into contact with each other after the wafer has passed through the gap to weld the aligned tubes together.

27. The method of claim 26 including controlling the movement of the ends toward each other in accordance with the movement of the wafer through the gap.

28. The method of claim 27 wherein the step of controlling the movement comprises providing an urging force to the holders to urge the holders toward each other, and limiting the movement of the holders toward each other by a contact member on each holder contacting an edge on the movable mounting unit on which the wafer is mounted while the wafer passes through the gap.

29. The method of claim 28 including maintaining the ends of the tubes in the area of the wafer in a pulsating manner.

30. The method of claim 26 including pre-cutting the ends of the tubes before the wafer enters the gap.

31. The method of claim 26 wherein the tubes are bent and then mounted in the tube holders in a bend condition.

* * * * *